(12) United States Patent
Kano et al.

(10) Patent No.: US 11,718,809 B2
(45) Date of Patent: *Aug. 8, 2023

(54) LUBRICANT AND LUBRICATION COMPOSITION

(71) Applicant: DIC Corporation, Tokyo (JP)

(72) Inventors: Yusuke Kano, Sakura (JP); Hironobu Oki, Sakura (JP); Tomoki Dohi, Sakura (JP); Jianjun Yuan, Sakura (JP)

(73) Assignee: DIC Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/777,543

(22) PCT Filed: Dec. 7, 2020

(86) PCT No.: PCT/JP2020/045436
§ 371 (c)(1),
(2) Date: May 17, 2022

(87) PCT Pub. No.: WO2021/117666
PCT Pub. Date: Jun. 17, 2021

(65) Prior Publication Data
US 2022/0403277 A1 Dec. 22, 2022

(30) Foreign Application Priority Data
Dec. 9, 2019 (JP) .................. 2019-222049

(51) Int. Cl.
*C10M 103/06* (2006.01)
*C10M 125/22* (2006.01)
(Continued)

(52) U.S. Cl.
CPC ........ *C10M 103/06* (2013.01); *C10M 125/22* (2013.01); *C10M 2201/066* (2013.01);
(Continued)

(58) Field of Classification Search
CPC .............. C10M 103/06; C10M 125/22; C10M 2201/066; C10M 2201/0663;
(Continued)

(56) References Cited

U.S. PATENT DOCUMENTS 3,647,689 A * 3/1972 Groszek .................... C01G 1/12
508/108
2012/0149611 A1* 6/2012 Yamaguchi .......... C09D 175/04
508/202

FOREIGN PATENT DOCUMENTS

| CN | 103073060 A | 5/2013 |
| JP | 2013-144758 A | 7/2013 |
| JP | 2017-115920 A | 6/2017 |

OTHER PUBLICATIONS

Bell, R.E., Herfert, R.E, "Preparation and Characterization of a New Crystaline Form of Molybdenum Disulfide", J. Am. Chem. Soc., 1957, 79, 3351-54 (Year: 1957).*

(Continued)

*Primary Examiner* — James C Goloboy
(74) *Attorney, Agent, or Firm* — Locke Lord LLP; James E. Armstrong, IV; Nicholas J. DiCeglie, Jr.

(57) ABSTRACT

The present invention relates to a lubricant containing molybdenum sulfide particles, and the molybdenum sulfide particles contain molybdenum disulfide having a 3R crystal structure. The present invention relates to a lubricating composition containing molybdenum sulfide particles, which are the lubricant, and a base oil which is a mineral oil, a synthetic oil, or a partially synthetic oil.

6 Claims, 4 Drawing Sheets

(51) Int. Cl.
    *C10N 10/12*     (2006.01)
    *C10N 20/06*     (2006.01)
    *C10N 30/06*     (2006.01)

(52) U.S. Cl.
    CPC ............... *C10M 2201/0663* (2013.01); *C10M 2203/003* (2013.01); *C10N 2010/12* (2013.01); *C10N 2020/06* (2013.01); *C10N 2030/06* (2013.01)

(58) Field of Classification Search
    CPC .... C10M 2203/003; C10M 2203/1006; C10N 2010/12; C10N 2020/06; C10N 2030/06
    See application file for complete search history.

(56) References Cited

OTHER PUBLICATIONS

Dukhovskoi, E.A., Lobashev, B.P., Makarov, Y.V., Sarpov, N.I., Silin, A.A., "Lubricant Properties of Molybdenum Disulfide Diffusion Coatings with Various Crystalline Structures", Soviet materials science: a translation of Fiziko-khimicheskaya mekhanika materialov, 1975, 10, 44-46 (Year: 1975).*

* cited by examiner

SYNTHESIS EXAMPLE 1

[Fig. 7]

COMPARATIVE EXAMPLE 3

[Fig. 8]

LUBRICANT AND LUBRICATION COMPOSITION

TECHNICAL FIELD

The present invention relates to a lubricant and a lubricating composition.

The present application claims priority based on Japanese Patent Application No. 2019-222049 filed on Dec. 9, 2019 in Japan, and contents thereof are incorporated herein.

BACKGROUND ART

It is known that molybdenum sulfide typified by molybdenum disulfide ($MoS_2$) is applied as a lubricant contained in, for example, a solid sliding member and grease (see PTLs 1 and 2).

Figure 4:
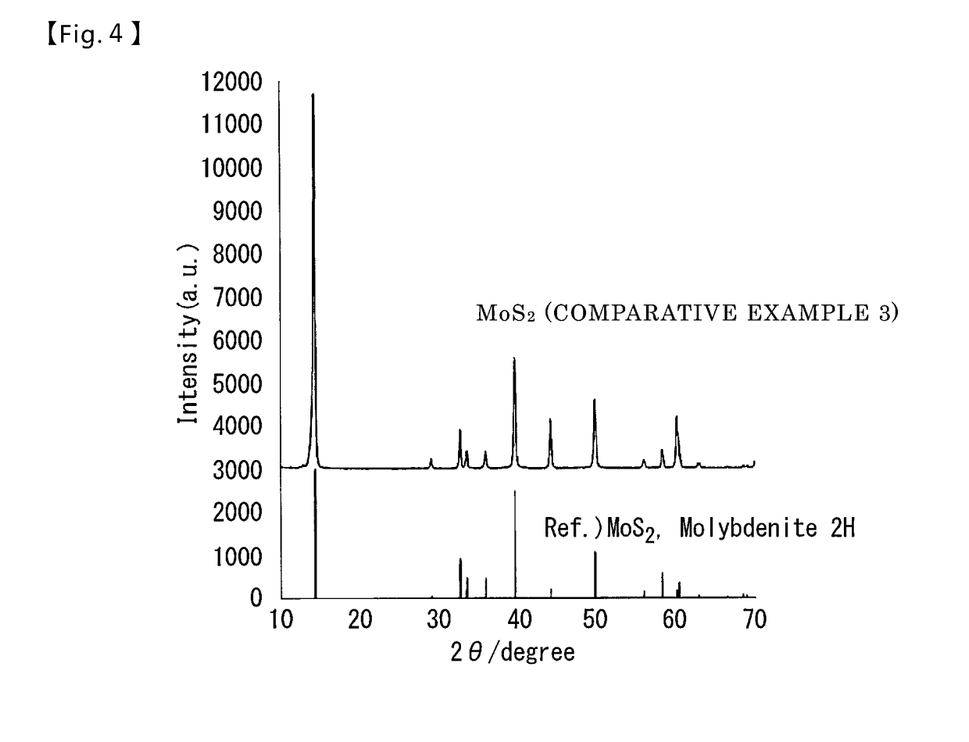
FIG. 4 shows a result of an X-ray diffraction (XRD) pattern of molybdenum sulfide particles according to Comparative Example 3 together with the diffraction pattern of the 2H crystal structure of molybdenum disulfide ($MoS_2$).

Molybdenum disulfide, which is generally used as a lubricant, is a hexagonal solid lubricant and has only a 2H crystal structure as α crystal structure as shown in FIG. 4.

CITATION LIST

Patent Literature

PTL 1: JP-A-2017-115920
PTL 2: JP-A-2013-144758

SUMMARY OF INVENTION

Technical Problem

Molybdenum disulfide ($MoS_2$) has excellent lubricating properties, and friction marks are less likely to be formed on a member to be slid. However, when a high load is applied, seizure may occur, and there is a demand for a lubricant by which seizure is less likely to occur even when a higher load is applied.

Therefore, an object of the present invention is to provide a lubricant and a lubricating composition containing molybdenum sulfide particles, by which seizure is less likely to occur even when a high load is applied.

Solution to Problem

The invention includes the following aspects.

[1] A lubricant containing molybdenum sulfide particles, in which
the molybdenum sulfide particles contain molybdenum disulfide having a 3R crystal structure.

[2] The lubricant according to the above [1], in which
the molybdenum sulfide particles contain molybdenum disulfide having a 2H crystal structure and a 3R crystal structure.

[3] The lubricant according to the above [2], in which
in a spectrum of the molybdenum sulfide particles obtained from powder X-ray diffraction (XRD) using Cu-Kα rays as an X-ray source, both a peak in a vicinity of 39.5° and a peak in a vicinity of 49.5° include a synthetic peak of the 2H crystal structure and the 3R crystal structure, and a half width is 1° or more.

[4] The lubricant according to any one of the above [1] to [3], in which
the molybdenum sulfide particles have a specific surface area of 10 $m^2/g$ or more, the specific surface area being measured by a BET method.

[5] The lubricant according to any one of the above [1] to [4], in which
the molybdenum sulfide particles have a median diameter $D_{50}$ of 10 nm to 1,000 nm, the median diameter $D_{50}$ being determined by a dynamic light scattering type particle diameter distribution measuring device.

[6] The lubricant according to any one of the above [1] to [5], in which
in a radial distribution function of the molybdenum sulfide particles obtained from an extended X-ray absorption fine structure (EXAFS) spectrum of a K absorption edge of molybdenum, a ratio (I/II) of peak intensity I caused by Mo—S to peak intensity II caused by Mo—Mo is more than 1.0.

[7] A lubricating composition comprising:
molybdenum sulfide particles which are the lubricant according to any one of the above [1] to [6]; and
a base oil which is a mineral oil, a synthetic oil, or a partially synthetic oil.

[8] The lubricating composition according to the above [7], in which
the molybdenum sulfide particles, which are the lubricant, are contained in an amount of 0.0001% by mass to 50% by mass with respect to 100% by mass of the total mass of the lubricating composition.

Advantageous Effects of Invention

The invention can provide a lubricant and a lubricating composition that are less likely to cause seizure even when a high load is applied.

DESCRIPTION OF EMBODIMENTS

<Lubricant>

A lubricant according to the present embodiment contains molybdenum sulfide particles. The molybdenum sulfide particles are contained, so that friction marks are less likely to be formed on a member to be slid.

Further, in the lubricant according to the present embodiment, the molybdenum sulfide particles contain molybdenum disulfide having a 3R crystal structure. Molybdenum disulfide, which is generally used as a lubricant, contains a large number of particles having a particle diameter of more than 1 μm. In addition, molybdenum disulfide is a hexagonal solid lubricant, and has only a 2H crystal structure as α crystal structure, as shown in FIG. 4. In contrast, as for the lubricant in which the molybdenum sulfide particles contain molybdenum disulfide having the 3R crystal structure, seizure is less likely to occur even when a high load is applied.

In the lubricant according to the present embodiment, the median diameter $D_{50}$ of the molybdenum sulfide particles is preferably 10 nm to 1,000 nm, and the median diameter $D_{50}$ is determined by a dynamic light scattering type particle diameter distribution measuring device.

Commercially available $MoS_2$ is a crushed product of ore, and contains a large number of particles having a particle diameter of more than 1 μm, which causes a small effect of a lubricant per weight, and precipitation of a lubricating composition containing a base oil having a small viscosity.

Regarding lubricant according to the present embodiment, the median diameter $D_{50}$ of the molybdenum sulfide particles is 1,000 nm or less, so that when the molybdenum sulfide particles are used as a lubricant, seizure is less likely to occur even when a high load is applied. This is because, when friction surfaces of members to be slid approach each other to a distance of less than 1 μm (that is, 1,000 nm) under a high load, the lubricant remains without being removed from this gap, and a lubricating performance can be continuously maintained. Further, the median diameter $D_{50}$ is 1,000 nm or less, so that, when the molybdenum sulfide particles are used for a lubricating composition containing a base oil, the molybdenum sulfide particles do not easily precipitate, and is excellent in storage stability.

Further, since the molybdenum sulfide particles that have become floating components due to the median diameter $D_{50}$ of 1,000 nm or less do not easily precipitate, even if the friction surfaces of the members to be slid are disposed perpendicularly or nearly perpendicularly in a state where one member to be slid is easily affected by the gravity of the other one, the molybdenum sulfide particles can be present in a state where the molybdenum sulfide particles have already entered the entire upper and lower gaps between the friction surfaces of the members to be slid at a time point before sliding. Therefore, it is considered that compared with molybdenum sulfide that easily precipitates according to the related art, the molybdenum sulfide particles can prevent, for example, particularly, scraping of an upper part at the start of sliding, and as a result, can contribute to extending the life of the friction surface of the member to be slid.

Further, it is considered that, when the lubricant according to the present embodiment is used, for example, in sliding of a plurality of metal balls as the members to be slid and the metal balls are slid and pressed against each other until a distance between the metal balls is less than 1 μm (that is, 1,000 nm) under a high load, the lubricant according to the present embodiment can remain in a gap without being removed from a clearance between the metal balls because the median diameter $D_{50}$ is as small as 1,000 nm or less, and a probability of contact between friction surfaces of the metal balls (or contact area×time) remains low, and seizure caused by rubbing is less likely to occur.

The median diameter $D_{50}$ of the molybdenum sulfide particles determined by the dynamic light scattering type particle diameter distribution measuring device is preferably 10 nm to 1,000 nm, more preferably 600 nm or less, still more preferably 500 nm or less, and most preferably 400 nm or less from the viewpoint of the above effects. The median diameter $D_{50}$ of the molybdenum sulfide particles may be 10 nm or more, 20 nm or more, or 40 nm or more.

The molybdenum sulfide particles preferably contain molybdenum disulfide having the 2H crystal structure and the 3R crystal structure. Molybdenum disulfide, which is generally used as a lubricant, contains a large number of particles having a particle diameter of more than 1 μm, is a hexagonal solid lubricant, and has only a 2H crystal structure as a crystal structure, as shown in FIG. 4. In contrast, molybdenum sulfide particles produced by a "method for producing molybdenum trioxide particles" and a "method for producing molybdenum sulfide particles" described later include the 2H crystal structure and the 3R crystal structure, and the median diameter $D_{50}$ can be easily adjusted to 10 nm to 1,000 nm.

Further, it is preferable that, in a spectrum of the molybdenum sulfide particles obtained from the powder X-ray diffraction (XRD) using Cu-Kα rays as an X-ray source, both a peak in the vicinity of 39.5° and a peak in the vicinity of 49.5° include a synthetic peak of the 2H crystal structure and the 3R crystal structure, and a half width is 1° or more. Further, the molybdenum sulfide particles may have α crystal structure other than the 2H crystal structure and the 3R crystal structure of molybdenum disulfide, such as a 1H crystal structure.

The molybdenum sulfide particles having the 3R crystal structure as a metastable structure can be distinguished by the fact that, in the spectrum obtained from the powder X-ray diffraction (XRD) using the Cu-Kα rays as the X-ray source, both the peak in the vicinity of 39.5° and the peak in the vicinity of 49.5° include the synthetic peak of the 2H crystal structure and the 3R crystal structure.

Primary particles of the molybdenum sulfide particles in a two-dimensional image when the molybdenum sulfide particles are imaged with a transmission electron microscope (TEM) may have a particle shape, a spherical shape, a plate shape, a needle shape, a string shape, a ribbon shape, or a sheet shape, or may have a combination of these shapes. The molybdenum sulfide preferably has a ribbon shape or a sheet shape. The shape of 50 primary particles of the molybdenum sulfide preferably has a size in the range of length (vertical)×width (horizontal)=50 nm to 1,000 nm×3 nm to 100 nm on average, more preferably a size in the range of 100 nm to 500 nm×5 nm to 50 nm, and particularly preferably a size in the range of 150 nm to 400 nm×10 nm to 20 nm. When the molybdenum sulfide has a ribbon shape or a sheet shape, a specific surface area of the molybdenum sulfide particles can be increased. Here, the ribbon shape or the sheet shape means a thin layer shape. An aspect ratio of the primary particles of the molybdenum sulfide, that is, a value of (length (size))/(height (depth)) is preferably 1.2 to 1,200, more preferably 2 to 800, still more preferably 5 to 400, and particularly preferably 10 to 200 on average of 50 particles.

It is considered that, since the primary particles of the molybdenum sulfide particles do not have a simple spherical shape, but have the ribbon shape or the sheet shape having a large aspect ratio, it can be expected to more efficiently cover the friction surfaces of the members to be slid that are about to come into contact with each other and reduce the probability (or contact area×time) of contact between the friction surfaces of the members to be slid, and the seizure caused by rubbing is less likely to occur.

The specific surface area of the molybdenum sulfide particles measured by a BET method is preferably 10 m²/g or more, more preferably 30 m²/g or more, and particularly preferably 40 m²/g or more. The specific surface area of the molybdenum sulfide particles measured by the BET method may be 300 m²/g or less, 200 m²/g or less, or 100 m²/g or less.

Layers constituting the primary particles of the molybdenum sulfide particles approach each other by a relatively weak interaction, and can be easily displaced from each other by an external force such as friction. Therefore, when the primary particles of the molybdenum sulfide particles are sandwiched between metals as the members to be slid, the layers constituting the primary particles are displaced by a frictional force, an apparent friction coefficient is lowered, and contact between the metals as members to be slid can also be prevented.

It is considered that, in a case where the specific surface area of the molybdenum sulfide particles measured by the BET method is as large as 10 m²/g or more, the contact area between the metals as the members to be slid can be further reduced when the primary particles are present between the metals as the members to be slid, and therefore, such molybdenum sulfide particles contribute to both improving a performance of the lubricant and preventing seizure.

In a radial distribution function of the molybdenum sulfide particles obtained from an extended X-ray absorption fine structure (EXAFS) spectrum of a K absorption edge of molybdenum, a ratio (I/II) of peak intensity I caused by Mo—S to peak intensity II caused by Mo—Mo is preferably more than 1.0, more preferably 1.1 or more, and particularly preferably 1.2 or more.

In the crystal structure of molybdenum disulfide, the distances between Mo and S are almost the same in the 2H crystal structure and the 3R crystal structure due to a covalent bond, so that the peak intensities caused by Mo—S are the same in the 2H crystal structure and the 3R crystal structure in the extended X-ray absorption fine structure (EXAFS) spectrum of the K absorption edge of molybdenum.

On the other hand, since the 2H crystal structure of molybdenum disulfide is hexagonal, a hexagon, which is the same as a hexagon of Mo atoms, is located 90° directly below the hexagon of Mo atoms, and thus the distance between Mo and Mo is shorter, and the peak intensity II caused by Mo—Mo is stronger.

Conversely, since the 3R crystal structure of molybdenum disulfide is rhombohedral, a hexagon, which is not just below 90° but half offset from a hexagon, is present, and thus the distance between Mo and Mo is longer, and the peak intensity II caused by Mo—Mo is weaker.

The ratio (I/II) is smaller in a pure 2H crystal structure of molybdenum disulfide, but the ratio (I/II) is larger as molybdenum disulfide has the 3R crystal structure.

In the 3R crystal structure, since respective hexagons of the Mo atoms in three layers are offset from each other by half of the hexagon, it can be expected that the interaction between the layers is small and slipping occurs readily compared with the 2H crystal structure in which hexagons of Mo atoms in two layers are arranged vertically and regularly.

Since the presence of molybdenum trioxide is considered to adversely influence the lubricating performance, the conversion rate $R_C$ to $MoS_2$ of the molybdenum sulfide particles is preferably 70% or more, more preferably 80% or more, and particularly preferably 90% or more.

Since the molybdenum sulfide particles have a large conversion rate $R_C$ to $MoS_2$, the molybdenum sulfide particles can not only exhibit the lubricating performance by heating caused by friction but also have lubricating properties better than that of other molybdenum disulfide members or precursors thereof which may generate molybdenum trioxide as a by-product or may contain molybdenum trioxide.

The conversion rate $R_C$ to $MoS_2$ of the molybdenum sulfide particles can be determined by a reference intensity ratio (RIR) method based on spectral data obtained by measuring the molybdenum sulfide particles with the X-ray diffraction (XRD). Using an RIR value $K_A$ of molybdenum sulfide ($MoS_2$), integrated intensity $I_A$ of a peak in the vicinity of 2θ=14.4°±0.5° attributed to the (002) plane or the (003) plane of molybdenum sulfide ($MoS_2$), an RIR value $K_B$ of each molybdenum oxide ($MoO_3$ as a raw material, and $Mo_9O_{25}$, $Mo_4O_{11}$, $MoO_2$, etc. as reaction intermediates), and integrated intensity $I_B$ of the strongest line peak of each molybdenum oxide ($MoO_3$ as a raw material, and $Mo_9O_{25}$, $Mo_4O_{11}$, $MoO_2$, etc. as reaction intermediates), the conversion rate $R_C$ to $MoS_2$ can be determined according to the following equation (1).

$$R_C(\%)=(I_A/K_A)/(\Sigma(I_B/K_B))\times100 \tag{1}$$

Here, values described in the inorganic crystal structure database (ICSD) (created by Japan Association for International Chemical Information) can be used as the RIR values, and integrated powder X-ray analysis software (PDXL) (produced by Rigaku Corporation) can be used for analysis.

<Method for Producing Molybdenum Sulfide Particles>

The molybdenum sulfide particles can be produced, for example, by heating molybdenum trioxide particles which contain primary particles having an average particle diameter of 5 nm to 1,000 nm in the presence of a sulfur source at a temperature of 200° C. to 1,000° C.

The average particle diameter of the primary particles of the molybdenum trioxide particles refers to an average value of primary particle diameters of 50 primary particles randomly selected when the molybdenum trioxide particles are imaged with a scanning electron microscope (SEM), the major axis (the Feret diameter of the longest portion observed) and the minor axis (the short Feret diameter in a direction perpendicular to the Feret diameter of the longest portion) of the particles (that is, the primary particles) as minimum units constituting aggregates on a two-dimensional image are measured, and an average value thereof is defined as the primary particle diameter.

Molybdenum oxide particles used for producing the molybdenum sulfide particles preferably include an aggregate of primary particles containing molybdenum trioxide having a β crystal structure. The molybdenum oxide particles have better reactivity with sulfur than molybdenum trioxide particles having only α crystals as a crystal structure in the related art, and contain molybdenum trioxide having a β crystal structure, so that the conversion rate $R_C$ to $MoS_2$ can be increased in a reaction with the sulfur source.

The β crystal structure of molybdenum trioxide can be confirmed by the presence of a peak (in the vicinity of 2θ: 23.01°, No. 86426 (inorganic crystal structure database (ICSD))) attributed to the (011) plane of a β crystal of MoO₃ in a spectrum obtained from the powder X-ray diffraction (XRD) using the Cu-Kα rays as the X-ray source. An α crystal structure of molybdenum trioxide can be confirmed by the presence of a peak of the (021) plane (in the vicinity of 2θ: 27.32°, No. 166363 (inorganic crystal structure database (ICSD))) of an α crystal of MoO₃.

Examples of the sulfur source include sulfur and hydrogen sulfide, which may be used alone or in combination of two.

The method for producing the molybdenum sulfide particles may include heating the molybdenum trioxide particles including the aggregate of the primary particles containing molybdenum trioxide having the β crystal structure at a temperature of 100° C. to 800° C. in the absence of the sulfur source, and then heating the molybdenum trioxide particles at a temperature of 200° C. to 1,000° C. in the presence of the sulfur source.

The time of heating in the presence of the sulfur source may be 1 to 20 hours, 2 to 15 hours, or 3 to 10 hours as long as the sulfurization reaction proceeds sufficiently.

In the method for producing molybdenum sulfide particles, the feed ratio of the amount of S in the sulfur source to the amount of MoO₃ in the molybdenum trioxide particles is preferably set under conditions under which the sulfurization reaction proceeds sufficiently. With respect to 100 mol % of the amount of MoO₃ in the molybdenum trioxide particles, the amount of S in the sulfur source is preferably 500 mol % or more, more preferably 600 mol % or more, and particularly preferably 700 mol % or more. With respect to 100 mol % of the amount of MoO₃ in the molybdenum trioxide particles, the amount of S in the sulfur source may be 3,000 mol % or less, 2,000 mol % or less, or 1,500 mol % or less.

In the method for producing molybdenum sulfide particles, the temperature of heating in the presence of the sulfur source may be a temperature at which the sulfurization reaction proceeds sufficiently, and is preferably 320° C. or higher, more preferably 340° C. or higher, and particularly preferably 360° C. or higher. The heating temperature may be 320° C. to 1,000° C., 340° C. to 1,000° C., or 360° C. to 500° C.

In the method for producing molybdenum sulfide particles, the average particle diameter of the primary particles of the molybdenum trioxide particles is preferably 1 μm or less. From the viewpoint of the reactivity with sulfur, the average particle diameter is more preferably 600 nm or less, still more preferably 400 nm or less, and particularly preferably 200 nm or less. The average particle diameter of the primary particles of the molybdenum trioxide particles may be 10 nm or more, 20 nm or more, or 40 nm or more.

In the method for producing molybdenum sulfide particles, the molybdenum trioxide particles preferably have a MoO₃ content of 99.6% or more as measured by an X-ray fluorescent (XRF). Accordingly, the conversion rate $R_C$ to MoS₂ can be increased, and a molybdenum sulfide which has high purity and has no risk of generating sulfides derived from impurities and which has good storage stability can be obtained.

In the method for producing molybdenum sulfide particles, as for the molybdenum trioxide particles, a ratio (β (011)/α (021)) of an intensity of a peak attributed to the (011) plane of the β crystal of MoO₃ to an intensity of a peak attributed to the (021) plane of the a crystal of MoO₃ is preferably 0.1 or more in the spectrum obtained from the powder X-ray diffraction (XRD) using the Cu-Kα rays as the X-ray source.

From the intensity of the peak attributed to the (011) plane of the β crystal of MoO₃ and the intensity of the peak attributed to the (021) plane of the α crystal of MoO₃, the maximum intensity of each peak is read to obtain the ratio (β (011)/α (021)).

In the molybdenum trioxide particles, the ratio (β (011)/α (021)) is preferably 0.1 to 10.0, more preferably 0.2 to 10.0, and particularly preferably 0.4 to 10.0.

The molybdenum trioxide particles preferably have a specific surface area of 10 m²/g to 100 m²/g, and the specific surface area is measured by the BET method.

In the molybdenum trioxide particles, the specific surface area is preferably 10 m²/g or more, more preferably 20 m²/g or more, and still more preferably 30 m²/g or more from the viewpoint of improving the reactivity with sulfur. In the molybdenum trioxide particles, the specific surface area is preferably 100 m²/g or less, and may be 90 m²/g or less or 80 m²/g or less from the viewpoint of facilitation in production.

In the molybdenum trioxide particles, a ratio (I/II) of peak intensity I caused by Mo—O to peak intensity II caused by Mo—Mo is preferably more than 1.1 in the radial distribution function obtained from the extended X-ray absorption fine structure (EXAFS) spectrum of the K absorption edge of molybdenum.

As for the peak intensity I caused by Mo—O and the peak intensity II caused by Mo—Mo, the maximum intensity of each peak is read to obtain the ratio (I/II). The ratio (I/II) is considered to indicate that the β crystal structure of MoO₃ is obtained in the molybdenum trioxide particles, and a greater ratio (I/II) indicates better reactivity with sulfur.

In the molybdenum trioxide particles, the ratio (I/II) is preferably 1.1 to 5.0, and may be 1.2 to 4.0 or 1.2 to 3.0.

(Method for Producing Molybdenum Trioxide Particles)

The molybdenum trioxide particles can be produced by vaporizing a molybdenum oxide precursor compound to form molybdenum trioxide vapor and cooling the molybdenum trioxide vapor.

The method for producing molybdenum trioxide particles includes calcining a raw material mixture containing a molybdenum oxide precursor compound and a metal compound other than the molybdenum oxide precursor compound to vaporize the molybdenum oxide precursor compound so as to form molybdenum trioxide vapor. The ratio of the metal compound to 100% by mass of the raw material mixture is preferably 70% by mass or less in terms of an oxide.

Figure 1:
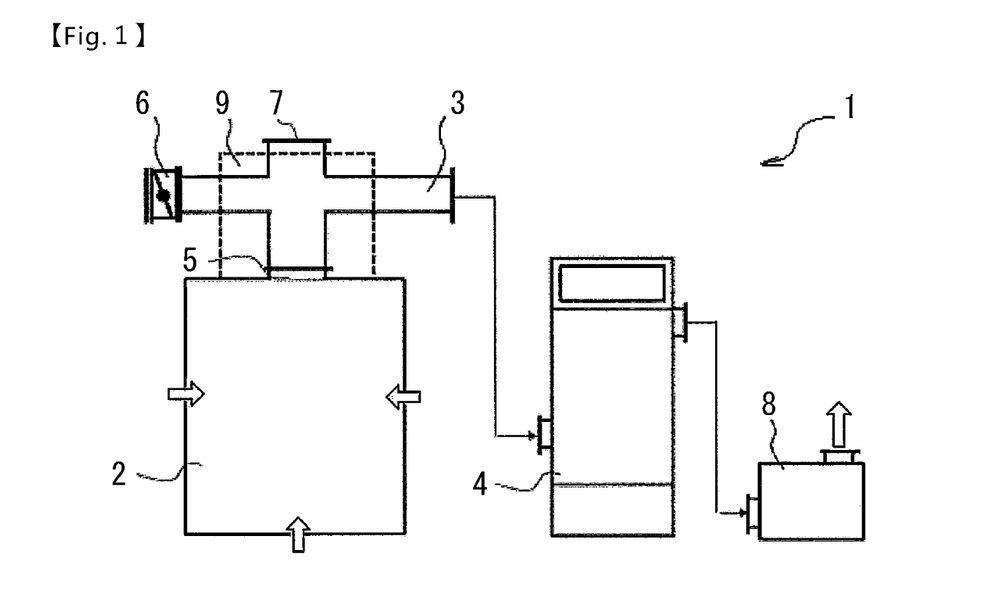
FIG. 1 is a schematic view of an example of an apparatus used for producing molybdenum trioxide particles serving as a raw material of molybdenum sulfide particles according to Synthesis Example 1.

The method for producing molybdenum trioxide particles can be preferably carried out by using a production apparatus 1 shown in FIG. 1.

FIG. 1 is a schematic view of an example of an apparatus used for producing the molybdenum trioxide particles. The production apparatus 1 includes a calcining furnace 2 for calcining a molybdenum oxide precursor compound or the raw material mixture to vaporize the molybdenum oxide precursor compound, a cross-shaped cooling pipe 3 which is connected to the calcining furnace 2 and by which the molybdenum trioxide vapor obtained by the vaporization in the calcining is formed into particles, and a collection device 4 as a collection unit for collecting molybdenum trioxide particles obtained by the particle formation in the cooling pipe 3. At this time, the calcining furnace 2 and the cooling pipe 3 are connected to each other via a discharge port 5. Further, in the cooling pipe 3, an opening degree adjustment damper 6 is disposed at an outside air intake port (not shown) at a left end portion, and an observation window 7 is disposed at an upper end portion. An air-exhaust device 8, which is a first air blowing unit, is connected to the collection device 4. When the air-exhaust device 8 discharges air, the air in the collection device 4 and the cooling pipe 3 is sucked, and the outside air is blown into the cooling pipe 3 from the opening degree adjustment damper 6 of the cooling pipe 3. That is, the air-exhaust device 8 passively blows air to the cooling pipe 3 by exhibiting a suction function. In addition, the production apparatus 1 may include an external cooling device 9, so that cooling conditions of the molybdenum trioxide vapor generated from the calcining furnace 2 can be freely controlled.

The opening degree adjustment damper 6 takes in air from the outside air intake port and the molybdenum trioxide vapor obtained by the vaporization in the calcining furnace 2 is cooled in an air atmosphere to obtain molybdenum trioxide particles, so that the ratio (I/II) can be made more than 1.1, and the β crystal structure of $MoO_3$ can be easily obtained in the molybdenum trioxide particles. When the molybdenum trioxide vapor is cooled in a state where a concentration of oxygen in a nitrogen atmosphere is low, for example, when the molybdenum trioxide vapor is cooled using liquid nitrogen, the oxygen defect density is likely to increase and the ratio (I/II) is likely to decrease.

The molybdenum oxide precursor compound is preferably a precursor compound for forming the molybdenum trioxide particles including an aggregate of the primary particles containing molybdenum trioxide having a β crystal structure.

The molybdenum oxide precursor compound is not particularly limited as long as it forms molybdenum trioxide vapor by being calcined, and examples thereof include metal molybdenum, molybdenum trioxide, molybdenum dioxide, and molybdenum sulfide. As the molybdenum oxide precursor compound, commercially available α-crystal molybdenum trioxide is preferably used. Further, when ammonium molybdate is used as the molybdenum oxide precursor compound, the ammonium molybdate is converted, by calcining, into molybdenum trioxide that is thermodynamically stable, and thus the molybdenum oxide precursor compound to be vaporized becomes molybdenum trioxide.

The molybdenum trioxide vapor can also be formed by calcining a raw material mixture containing a molybdenum oxide precursor compound and a metal compound other than the molybdenum oxide precursor compound.

The metal compound other than the molybdenum oxide precursor compound is not particularly limited, and examples thereof include an aluminum compound, a silicon compound, a titanium compound, a magnesium compound, a sodium compound, a potassium compound, a zirconium compound, an yttrium compound, a zinc compound, a copper compound, and an iron compound. Among these, it is preferable to use an aluminum compound, a silicon compound, a titanium compound, or a magnesium compound.

The molybdenum oxide precursor compound and the metal compound other than the molybdenum oxide precursor compound may form an intermediate, but even in this case, the intermediate is decomposed by calcining, and molybdenum trioxide can be vaporized in a thermodynamically stable form.

Among these compounds used as the metal compound other than the molybdenum oxide precursor compound, an aluminum compound is preferably used to prevent damage to a calcining furnace, and in order to improve the purity of the molybdenum trioxide particles, the metal compound other than the molybdenum oxide precursor compound may not be used.

Examples of the aluminum compound include aluminum chloride, aluminum sulfate, basic aluminum acetate, aluminum hydroxide, boehmite, pseudo-boehmite, transition aluminum oxides (γ-aluminum oxide, δ-aluminum oxide, θ-aluminum oxide, etc.), α-aluminum oxide, and a mixed aluminum oxide having two or more crystal phases.

When a raw material mixture containing a molybdenum oxide precursor compound and a metal compound other than the molybdenum oxide precursor compound is calcined, the content of the molybdenum oxide precursor compound is preferably 40% by mass to 100% by mass, and may be 45% by mass to 100% by mass or 50% by mass to 100% by mass with respect to 100% by mass of the raw material mixture.

The calcining temperature varies depending on the molybdenum oxide precursor compound and the metal compound to be used, the desired molybdenum trioxide particles and the like, and is usually preferably a temperature at which the intermediate can be decomposed. For example, since aluminum molybdate can be formed as an intermediate when a molybdenum compound is used as the molybdenum oxide precursor compound and an aluminum compound is used as the metal compound, the calcining temperature is preferably 500° C. to 1,500° C., more preferably 600° C. to 1,550° C., and still more preferably 700° C. to 1,600° C.

The calcining time is not particularly limited, and may be, for example, 1 minute to 30 hours, 10 minutes to 25 hours, or 100 minutes to 20 hours.

The temperature rising rate varies depending on the properties of the molybdenum oxide precursor compound and the metal compound to be used, and the desired molybdenum trioxide particles, and the like, and is preferably 0.1° C./min to 100° C./min, more preferably 1° C./min to 50° C./min, and still more preferably 2° C./min to 10° C./min from the viewpoint of production efficiency.

The internal pressure in the calcining furnace is not particularly limited, and may be a positive pressure or a reduced pressure, but from the viewpoint of preferably discharging the molybdenum oxide precursor compound from the calcining furnace to the cooling pipe, the calcining is preferably performed under a reduced pressure. Specifically, the degree of pressure reduction is preferably −5,000 Pa to −10 Pa, more preferably −2,000 Pa to −20 Pa, and still more preferably −1,000 Pa to −50 Pa. The degree of pressure reduction of −5,000 Pa or more is preferable since high airtightness and mechanical strength of the calcining furnace are not excessively required, and production costs can be reduced. On the other hand, the degree of pressure reduction of −10 Pa or less is preferable since clogging of the molybdenum oxide precursor compound at a discharge port of the calcining furnace can be prevented.

When a gas is blown into the calcining furnace during calcining, the temperature of the blown gas is preferably 5° C. to 500° C., and more preferably 10° C. to 100° C.

Further, the blowing speed of the gas is preferably 1 L/min to 500 L/min, and more preferably 10 L/min to 200 L/min with respect to 100 L of an effective volume of the calcining furnace.

The temperature of the molybdenum trioxide vapor obtained by the vaporization varies depending on the type of the molybdenum oxide precursor compound to be used, and is preferably 200° C. to 2000° C., and more preferably 400° C. to 1,500° C. When the temperature of the molybdenum trioxide vapor obtained by the vaporization is 2,000° C. or lower, the vapor usually tends to be easily formed into particles by blowing outside air (0° C. to 100° C.) to the cooling pipe.

The discharge rate of the molybdenum trioxide vapor discharged from the calcining furnace can be controlled based on the amount of the molybdenum oxide precursor compound to be used, the amount of the metal compound to be used, the temperature of the calcining furnace, blowing of the gas into the calcining furnace, and the diameter of the discharge port of the calcining furnace. The discharge rate also varies depending on the cooling capacity of the cooling pipe, and the discharge rate of the molybdenum trioxide vapor discharged from the calcining furnace to the cooling pipe is preferably 0.001 g/min to 100 g/min, and more preferably 0.1 g/min to 50 g/min.

Further, the content of the molybdenum trioxide vapor contained in the gas discharged from the calcining furnace is preferably 0.01 mg/L to 1,000 mg/L, and more preferably 1 mg/L to 500 mg/L.

Next, the molybdenum trioxide vapor is cooled to form particles.

The molybdenum trioxide vapor is cooled by lowering the temperature of the cooling pipe. In this case, examples of a cooling method include cooling by blowing a gas into the cooling pipe as described above, cooling by a cooling mechanism of the cooling pipe, and cooling by an external cooling device.

The molybdenum trioxide vapor is preferably cooled in an air atmosphere. When the molybdenum trioxide vapor is cooled in an air atmosphere to form molybdenum trioxide particles, the ratio (I/II) can be made more than 1.1, and the β crystal structure of $MoO_3$ can be easily obtained in the molybdenum trioxide particles.

The cooling temperature (temperature of the cooling pipe) is not particularly limited, and is preferably −100° C. to 600° C., and more preferably −50° C. to 400° C.

The cooling rate of the molybdenum trioxide vapor is not particularly limited, and is preferably 100° C./s to 100,000° C./s, and more preferably 1,000° C./s to 50,000° C./s. As the cooling rate of the molybdenum trioxide vapor increases, molybdenum trioxide particles having a small particle diameter and a large specific surface area tend to be obtained.

When the cooling method is the cooling by blowing a gas into the cooling pipe, the temperature of the blown gas is preferably −100° C. to 300° C., and more preferably −50° C. to 100° C.

Further, the blowing speed of the gas is preferably 0.1 m³/min to 20 m³/min, and more preferably 1 m³/min to 10 m³/min. The blowing speed of the gas of 0.1 m³/min or more is preferable since a high cooling rate can be achieved, and clogging in the cooling pipe can be prevented. On the other hand, the blowing speed of the gas of 20 m³/min or less is preferable since the first air blowing unit (such as a blower) which is expensive is no longer needed, and production costs can be reduced.

The particles obtained by cooling the molybdenum trioxide vapor are transported to the collection device and are collected.

In the method for producing molybdenum trioxide particles, the particles obtained by cooling the molybdenum trioxide vapor may be calcined again at a temperature of 100° C. to 320° C.

That is, the molybdenum trioxide particles obtained by the method for producing molybdenum trioxide particles may be calcined again at a temperature of 100° C. to 320° C. The calcining temperature in the re-calcining may be 120° C. to 280° C. or 140° C. to 240° C. The calcining time in the re-calcining may be, for example, 1 minute to 4 hours, 10 minutes to 5 hours, or 100 minutes to 6 hours. However, a part of the β crystal structure of molybdenum trioxide disappears due to the re-calcining, and when calcining is performed at a temperature of 350° C. or higher for 4 hours, the β crystal structure of the molybdenum trioxide particles disappears, the ratio (β (011)/α (021)) is 0, and the reactivity with sulfur is impaired.

With the method for producing molybdenum trioxide particles described above, the molybdenum trioxide particles suitable for producing the molybdenum sulfide particles can be produced.

<Lubricating Composition>

A lubricating composition according to the present embodiment contains molybdenum sulfide particles which are the lubricant and a base oil which is a mineral oil, a synthetic oil, or a partially synthetic oil.

The base oil, which is a mineral oil, includes an oil obtained by rock drilling, an oil obtained from a plant or an animal, and mixtures thereof, for example, examples of such an oil include, but are not limited to, castor oil, lard oil, olive oil, peanut oil, corn oil, soybean oil, linseed oil, liquid petroleum, and paraffinic, naphthenic, or paraffin-naphthene mixed base oil. Such a base oil may be partially or completely hydrogenated, if desired.

Examples of the base oil, which is a synthetic oil, include a polyalphaolefin-based base oil, a hydrocarbon-based base oil, an ester-based base oil, an ether-based base oil, a silicone-based base oil, an alkylnaphthalene-based base oil, or a perfluoroalkylpolyether-based base oil.

The base oil, which is a partially synthetic oil, means a base oil obtained by mixing these mineral oils and synthetic oils.

In the lubricating composition, as the base oil, a base oil generally used for a lubricating composition can be used without limitation.

The kinematic viscosity of the base oil used in the lubricating composition according to the present embodiment at 40° C. may be 10 to 1,000 mm²/s, 20 to 500 mm²/s, 30 to 200 mm²/s, or 40 to 150 mm²/s. In the lubricating composition according to the present embodiment, since the median diameter $D_{50}$ of the molybdenum sulfide particles determined by the dynamic light scattering type particle diameter distribution measuring device is as small as 10 to 1,000 nm, precipitation of the molybdenum sulfide particles can be prevented even if a base oil having a relatively low viscosity is used.

The lubricating composition preferably contains 0.0001% by mass to 50% by mass, more preferably 0.01% by mass to 10% by mass, and particularly preferably 0.1% by mass to 5% by mass of the molybdenum sulfide particles, which are the lubricant, with respect to 100% by mass of the total mass of the lubricating composition.

The lubricating composition may further contain known additives such as a detergent, a viscosity modifier, a foaming inhibitor, a corrosion inhibitor, a rust inhibitor, an antioxidant, an anti-wear agent, and a friction modifier.

The lubricating composition can further contain a known dispersant contained in a general lubricating oil. The presence of the dispersant ensures the storage stability by further suppressing precipitation.

EXAMPLES

Next, the invention will be described in more detail with reference to Examples, but the invention is not limited to the following Examples.

[Method for Measuring Average Particle Diameter of Primary Particles of Molybdenum Trioxide Particles]

The molybdenum trioxide particles were imaged with a scanning electron microscope (SEM). The major axis (the Feret diameter of the longest portion observed) and the minor axis (the short Feret diameter in a direction perpendicular to the Feret diameter of the longest portion) of the particles (that is, primary particles) as the minimum units constituting aggregates on a two-dimensional image were measured, and an average value thereof was defined as the primary particle diameter. The same operation was performed on 50 primary particles randomly selected, and the average particle diameter of the primary particles was calculated based on the average value of the primary particle diameters of these primary particles.

[Purity Measurement of Molybdenum Trioxide: XRF Analysis]

About 70 mg of a sample of the collected molybdenum trioxide particles was taken on a filter paper and covered with a PP film, and the composition of the molybdenum trioxide particles was analyzed using an X-ray fluorescence analyzer Primus IV (manufactured by Rigaku Corporation). The amount of molybdenum determined based on an XRF analysis result was determined in terms of molybdenum trioxide (% by mass) with respect to 100% by mass of the molybdenum trioxide particles.

[Crystal Structure Analysis: XRD Method]

A sample of the collected molybdenum trioxide particles or a sulfide thereof was filled in a holder for a measurement sample having a depth of 0.5 mm, the holder was set in a wide-angle X-ray diffraction (XRD) apparatus (Ultima IV manufactured by Rigaku Corporation), and the sample was subjected to measurement under conditions of Cu/Kα rays, 40 kV/40 mA, a scanning speed of 2 degrees/minute, and a scanning range of 10 degrees or more and 70 degrees or less.

[Measurement of Specific Surface Area: BET Method]

A sample of the molybdenum trioxide particles or the molybdenum sulfide particles was measured with a specific surface area meter (BELSORP-mini manufactured by MicrotracBEL Corp.), and the surface area per gram of the sample measured based on the amount of the adsorbed nitrogen gas by the BET method was calculated as the specific surface area ($m^2/g$).

[Conversion Rate $R_C$ to $MoS_2$]

Molybdenum sulfide particles as a black powder were measured by X-ray diffraction (XRD). Next, using the RIR value $K_A$ of molybdenum sulfide ($MoS_2$), the integrated intensity $I_A$ of the peak in the vicinity of $2\theta=14.4°\pm0.5°$ attributed to the (002) plane or the (003) plane of molybdenum sulfide ($MoS_2$), the RIR value $K_B$ of each molybdenum oxide ($MoO_3$ as a raw material, and $Mo_9O_{25}$, $Mo_4O_{11}$, $MoO_2$, etc. as reaction intermediates), and the integrated intensity $I_B$ of the strongest line peak of each molybdenum oxide ($MoO_3$ as a raw material, and $Mo_9O_{25}$, $Mo_4O_{11}$, $MoO_2$, etc. as reaction intermediates), the conversion rate $R_C$ to $MoS_2$ was determined, based on the reference intensity ratio (RIR) method, according to the following equation (1).

$$R_C(\%) = (I_A/K_A)/(\Sigma(I_B/K_B)) \times 100 \tag{1}$$

Here, values described in the inorganic crystal structure database (ICSD) were used as the RIR values, and integrated powder X-ray analysis software (PDXL) (produced by Rigaku Corporation) was used for analysis.

[Measurement of Extended X-Ray Absorption Fine Structure (EXAFS)]

36.45 mg of a molybdenum sulfide powder and 333.0 mg of boron nitride were mixed in a mortar. 123.15 mg of the mixture was weighed and compressed and molded into a tablet having a diameter of 8 mm to obtain a measurement sample. Using the measurement sample, the extended X-ray absorption fine structure (EXAFS) was measured by a transmission method with BL5S1 of Aichi Synchrotron Radiation Center. Athena (Internet <URL: https://brucerav-el.github.io/demeter/>) was used for the analysis.

[Measurement of Median Diameter $D_{50}$ of Molybdenum Sulfide Particles]

0.1 g of the molybdenum sulfide powder was added to 20 cc of acetone and subjected to an ultrasonic treatment in an ice bath for 4 hours, and then the concentration thereof was appropriately adjusted with acetone to a concentration within a measurable range of a dynamic light scattering type particle diameter distribution measuring device (Nanotrac Wave II manufactured by MicrotracBEL Corp.) to obtain a measurement sample. Using the measurement sample, the particle diameter distribution in the range of particle diameters of 0.0001 μm to 10 μm was measured by the dynamic light scattering type particle diameter distribution measuring device (Nanotrac Wave II manufactured by MicrotracBEL Corp.) to calculate the median diameter $D_{50}$.

In this case, for particles having a median diameter $D_{50}$ more than 10 μm (Comparative Example 3), similarly, a solution was adjusted, and the particle diameter distribution in the range of particle diameters of 0.015 μm to 500 μm was measured with a laser diffraction particle size distribution analyzer (SALD-7000 manufactured by Shimadzu Corporation) to calculate the median diameter $D_{50}$.

[Method for Observing Particle Shape of Molybdenum Sulfide Particles]

The molybdenum sulfide particles were imaged with a transmission electron microscope (JEOL JEM1400), and 50 primary particles in the field of view of a two-dimensional image were observed to determine whether the primary particles have a ribbon shape or a sheet shape.

(Production of Molybdenum Trioxide Particles Having β Crystal Structure)

1 kg of a transition aluminum oxide (activated alumina manufactured by Wako Pure Chemical Industries, Ltd., average particle diameter: 45 μm) and 1 kg of molybdenum trioxide (manufactured by TAIYO KOKO Co., Ltd.) were mixed with each other, and the mixture was then charged into a sagger and calcined at a temperature of 1,100° C. for 10 hours in the calcining furnace 2 of the production apparatus 1 shown in FIG. 1. During the calcining, outside air (blowing speed: 50 L/min, outside air temperature: 25° C.) was introduced from a side surface and a lower surface of the calcining furnace 2. Molybdenum trioxide was evaporated in the calcining furnace 2 and then cooled in the vicinity of the collection device 4 and deposited as particles. An RHK simulator (manufactured by Noritake Co., Ltd.) was used as the calcining furnace 2, and a VF-5N dust collector (manufactured by AMANO Corporation) was used as the collection device 4.

After calcining, 1.0 kg of aluminum oxide which is a blue powder, and 0.85 kg of the molybdenum trioxide particles collected by the collection device 4 were taken out from the sagger. As for the collected molybdenum trioxide particles, it was found that an average particle diameter of primary particles was 80 nm, and the purity of molybdenum trioxide was 99.7% in the X-ray fluorescent (XRF) measurement. The specific surface area (SA) of the molybdenum trioxide particles measured by a BET method was 44.0 $m^2/g$.

Figure 2:
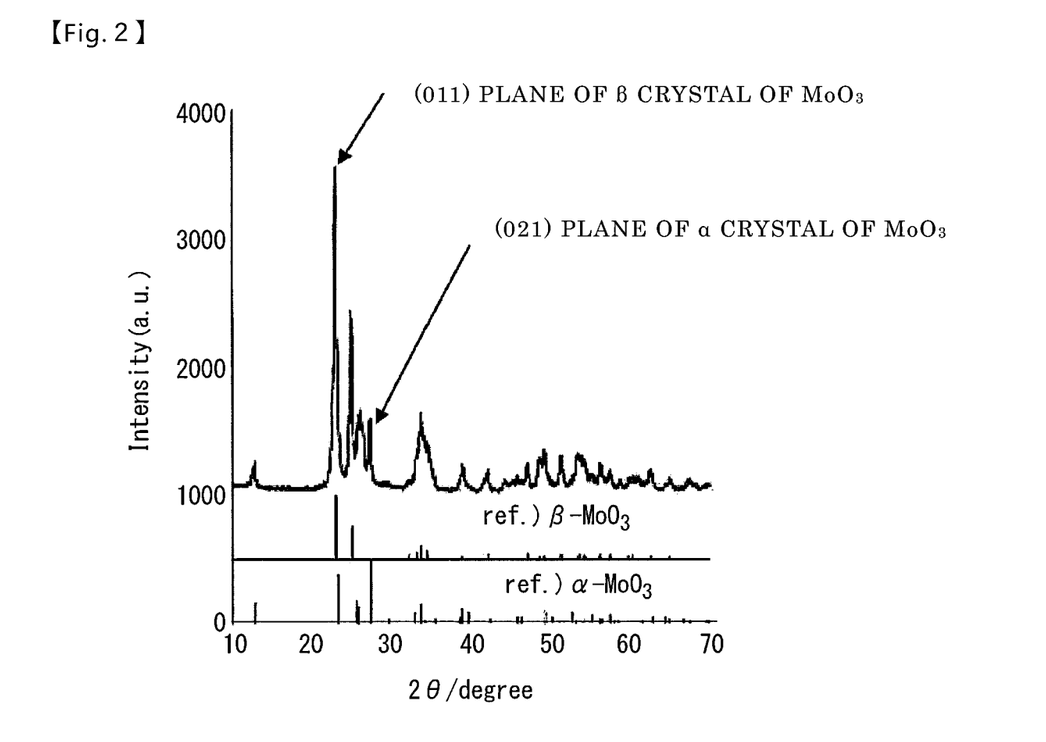
FIG. 2 shows a result of an X-ray diffraction (XRD) pattern of the molybdenum trioxide particles serving as a raw material of the molybdenum sulfide particles according to Synthesis Example 1 together with a standard pattern (α-$MoO_3$) of an α crystal and a standard pattern ((β-$MoO_3$) of a β crystal of molybdenum trioxide.

Further, X-ray diffraction (XRD) of the molybdenum trioxide particles was measured. The result of an X-ray diffraction pattern is shown in FIG. 2 together with a standard pattern of an α crystal of molybdenum trioxide and a standard pattern of a β crystal of molybdenum trioxide. A peak attributed to the α crystal of $MoO_3$ and a peak attributed to the β crystal of $MoO_3$ were observed, and no other peaks were observed. Next, a peak intensity ratio (β (011)/α (021)) of the (011) plane of the β crystal (in the vicinity of 2θ: 23.01°, No. 86426 (inorganic crystal structure database (ICSD))) and the (021) plane of the a crystal (in the vicinity of 2θ: 27.32°, No. 166363 (inorganic crystal structure database (ICSD))) was determined, and as a result, β (011)/α (021) was 5.2.

Synthesis Example 1

(Production of Molybdenum Sulfide Particles)

Figure 5:
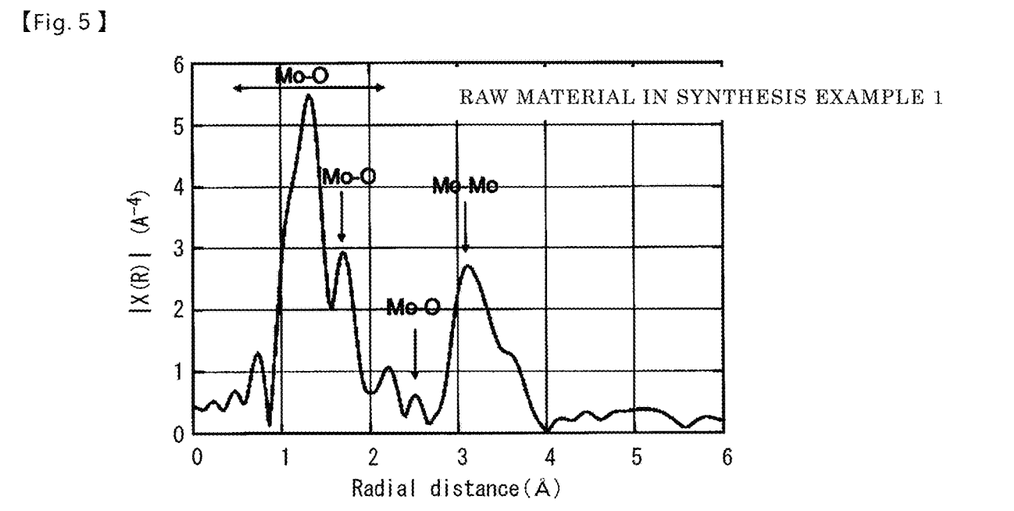
FIG. 5 is an extended X-ray absorption fine structure (EXAFS) spectrum of a K absorption edge of molybdenum measured using the molybdenum trioxide particles serving as a raw material of the molybdenum sulfide particles according to Synthesis Example 1.

32.76 mg of the molybdenum trioxide particles and 333.0 mg of boron nitride were mixed in a mortar. 121.92 mg of the mixture was weighed and compressed and molded into a tablet having a diameter of 8 mm, and an extended X-ray absorption fine structure (EXAFS) was measured. FIG. 5 shows an extended X-ray absorption fine structure (EXAFS) spectrum of a K absorption edge of molybdenum. In a radial distribution function obtained from the spectrum, the ratio (I/II) of the peak intensity I caused by Mo—O to the peak intensity II caused by Mo—Mo was 2.0.

Figure 3:
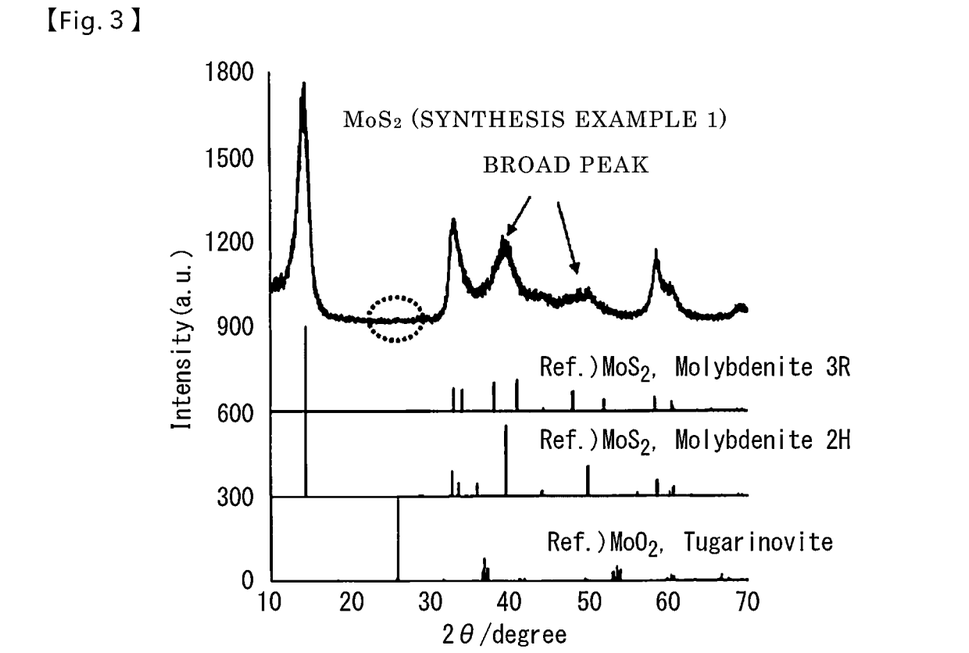
FIG. 3 shows a result of an X-ray diffraction (XRD) pattern of the molybdenum sulfide particles according to Synthesis Example 1 together with a diffraction pattern of a 3R crystal structure of molybdenum disulfide ($MoS_2$), a diffraction pattern of a 2H crystal structure of molybdenum disulfide ($MoS_2$), and a diffraction pattern of molybdenum dioxide ($MoO_2$).

In a porcelain crucible, 1.00 g of the molybdenum trioxide particles and 1.57 g of a sulfur powder (manufactured by Kanto Chemical Co., Ltd.) were mixed with each other with a stirring rod such that the powder was uniform, and the mixture was calcined in a nitrogen atmosphere at 500° C. for 4 hours to obtain a black powder. Here, the S amount of the sulfur is 705 mol % with respect to the $MoO_3$ amount of 100 mol % of the molybdenum trioxide particles. FIG. 3 shows a result of an X-ray diffraction (XRD) pattern of the black power (molybdenum sulfide particles according to Synthesis Example 1) together with a diffraction pattern of a 3R crystal structure of molybdenum disulfide ($MoS_2$), a diffraction pattern of a 2H crystal structure of molybdenum disulfide ($MoS_2$), and a diffraction pattern of molybdenum dioxide ($MoO_2$) which are described in the inorganic crystal structure database (ICSD). Molybdenum dioxide ($MoO_2$) is a reaction intermediate.

In the X-ray diffraction (XRD) pattern in FIG. 3, only peaks attributed to molybdenum disulfide ($MoS_2$) were detected, and a peak not attributed to molybdenum disulfide ($MoS_2$) was not observed. That is, no peaks of reaction intermediates such as molybdenum dioxide ($MoO_2$) that is a by-product were observed, and only a peak attributed to molybdenum disulfide ($MoS_2$) was observed, and thus it was found that the molybdenum sulfide particles according to Synthesis Example 1 had a conversion rate $R_C$ to $MoS_2$ of 99% or more, and the reaction with sulfur proceeded rapidly.

Crystal structure analysis of the molybdenum sulfide particles according to Synthesis Example 1 was performed by the X-ray diffraction (XRD), and as a result, it was found that a 2H crystal structure and a 3R crystal structure were included. Half widths of the peak in the vicinity of 39.5° and the peak in the vicinity of 49.5° were as wide as 2.36° and 3.71°, respectively.

The specific surface area of the molybdenum sulfide particles according to Synthesis Example 1 was measured by the BET method, and as a result, the specific surface area was 67.8 $m^2$/g.

The particle size distribution of the molybdenum sulfide particles according to Synthesis Example 1 was measured by a dynamic light scattering type particle diameter distribution measuring device to determine the median diameter $D_{50}$, and as a result, the median diameter $D_{50}$ was 170 nm.

Figure 6:
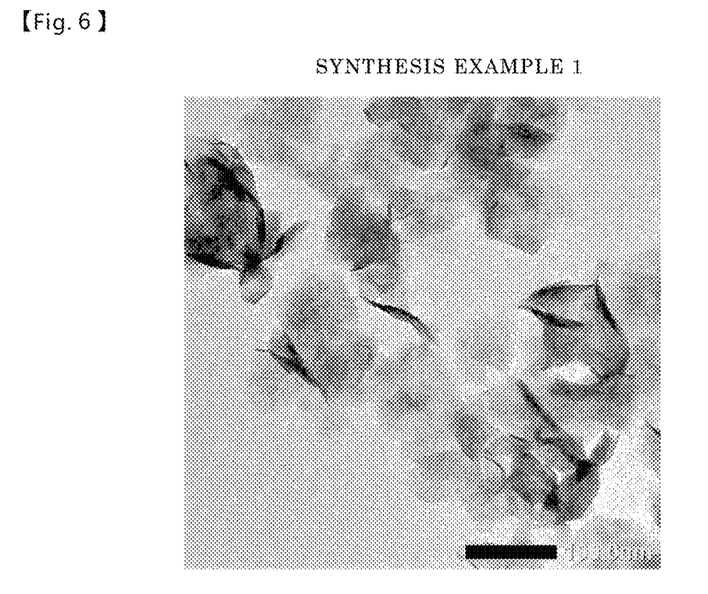
FIG. 6 is a TEM image of the molybdenum sulfide particles according to Synthesis Example 1.

FIG. 6 is a TEM image of the molybdenum sulfide particles according to Synthesis Example 1. It was observed that a large number of ribbon-shaped or sheet-shaped molybdenum sulfides having a size of about 200 nm were contained.

Figure 8:
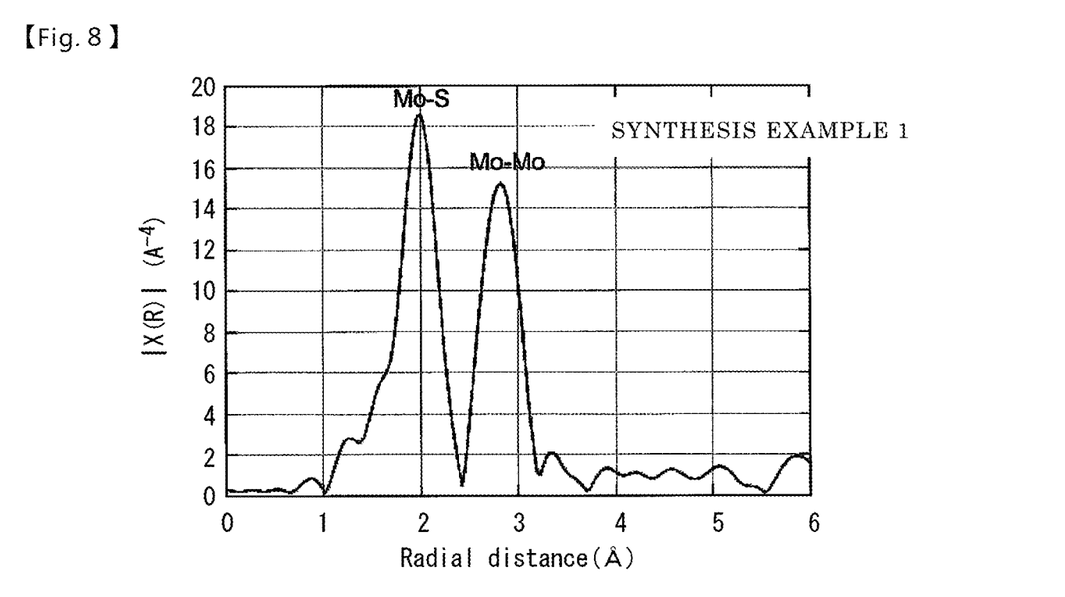
FIG. 8 is an extended X-ray absorption fine structure (EXAFS) spectrum of the K absorption edge of molybdenum measured using the molybdenum sulfide particles according to Synthesis Example 1.

The extended X-ray absorption fine structure (EXAFS) was measured using the molybdenum sulfide particles according to Synthesis Example 1. FIG. 8 shows an extended X-ray absorption fine structure (EXAFS) spectrum of a K absorption edge of molybdenum. In a radial distribution function obtained from the spectrum, the ratio (I/II) of the peak intensity I caused by Mo—S to the peak intensity II caused by Mo—Mo was 1.2.

(Dispersibility)

0.05 parts by mass of the molybdenum sulfide particles according to Synthesis Example 1, 0.5 parts by mass of a dispersant (Unidic R-2000PG manufactured by DIC Corporation), and 9.5 parts by mass of acetone were placed in a glass container and dispersed with an ultrasonic irradiation device for 7 hours. Then, the dispersion liquid was allowed to stand for 3 days, during which the light transmittance and the back light scattering intensity were measured in the vicinity of the center of the glass container using a stability tester (ST-1) (manufactured by EKO) to evaluate the precipitation of the particles, and as a result, none of the light transmittance and the back light scattering intensity changed, and the dispersibility of the molybdenum sulfide particles according to Synthesis Example 1 in a low-viscosity liquid was evaluated as "A" (good).

Example 1

1 part by mass of the molybdenum sulfide particles according to Synthesis Example 1 and 19 parts by mass of Cosmo Pure Spin D (manufactured by Cosmo Oil Lubricants Co., Ltd., kinematic viscosity at 40° C.: 6.5 $mm^2$/s) were placed in a container and dispersed with an ultrasonic irradiation device for 7 hours. 30 parts by mass of Diana Fresia (registered trademark) W-90 (manufactured by Idemitsu Kosan Co., Ltd., kinematic viscosity at 40° C.: 95 $mm^2$/s) was added to 20 parts by mass of the obtained dispersion liquid as a base oil, and the mixture was further dispersed by an ultrasonic treatment device for 1 hour to prepare a lubricating composition according to Example 1 containing a dispersion liquid.

(Shell Four-Ball Load Carrying Capacity Test)

The lubricating composition according to Example 1 was subjected to a shell four-ball load carrying capacity test by a method compliant with ASTM D2783 using a four-ball tester (Plint) manufactured by Phoenix Tribology Products. Specifically, the following two test methods (Test A) and (Test B) were carried out.

(Test A)

Three stainless steel balls having a diameter of ½ inch were fixed to the bottom of a sample container, and the lubricating composition according to Example 1 was placed in the sample container. One stainless steel ball was pressed against the top of the center of the three stainless steel balls and brought into contact with the three stainless steel balls at three points. A load of 32 kgf was applied vertically and downward from the top of the one stainless steel ball at the top to rotate the stainless steel ball at a speed of 1770 rpm for 10 seconds, and as a result, no friction marks having a width of 0.4 mm or more in either the vertical or horizontal direction were observed on the stainless steel balls.

Next, the above-described stainless steel balls were replaced with new balls, the lubricating composition according to Example 1 was cleaned and replaced using the lubricating composition from the same bottle, and a load of 40 kgf was applied to rotate the stainless steel ball at a speed of 1770 rpm for 10 seconds, and as a result, no friction marks having a width of 0.4 mm or more in either the vertical or horizontal direction were observed on the stainless steel balls.

Further, similarly, the above-described stainless steel balls were replaced with new balls, the lubricating composition according to Example 1 was cleaned and replaced using a lubricating composition from the same bottle, and the load was changed to 50 kgf, 63 kgf, and 80 kgf to carry out the test, and as a result, no friction marks having a width of 0.4 mm or more in either the vertical or horizontal direction were observed on the stainless steel balls.

Further, similarly, the above-described stainless steel balls were replaced with new balls, the lubricating composition according to Example 1 was cleaned and replaced using a lubricating composition from the same bottle, and a load of 100 kgf was applied to rotate the stainless steel ball at a speed of 1770 rpm for 10 seconds, and as a result, friction marks having a width of 0.4 mm or more in either the vertical or horizontal direction were observed on the stainless steel balls.

That is, the maximum load at which no friction marks having a width of 0.4 mm or more in either the vertical or horizontal direction appeared on the stainless steel balls was 80 kgf. That is, the evaluation result of the friction mark load was "A" (good).

(Test B)

After that, similarly, the above-described stainless steel balls were replaced with new balls, the lubricating composition according to Example 1 was cleaned and replaced using the lubricating composition from the same bottle, and a load of 100 kgf was applied to rotate the stainless steel ball at a speed of 1770 rpm for 10 seconds, and as a result, seizure did not occur on the stainless steel balls.

Further, similarly, the test was carried out by changing the load to 200 kgf, 300 kgf, 400 kgf, and 500 kgf, and this operation was repeated until the friction surfaces of the stainless steel balls were fused to each other and seizure occurred. The maximum load at which seizure did not occur was 400 kgf. That is, the evaluation result of the seizure load was "A" (good).

Comparative Example 1

Diana Fresia (registered trademark) W-90 (manufactured by Idemitsu Kosan Co., Ltd., kinematic viscosity at 40° C.: 95 mm$^2$/s) was used as a lubricating oil according to Comparative Example 1, and a shell four-ball load carrying capacity test was carried out in the same manner as in Example 1. In (Test A), the maximum load at which no friction marks having a width of 0.4 mm or more appeared was 40 kgf. In (Test B), the maximum load at which seizure did not occur was 130 kgf. That is, the evaluation result of the friction mark load was "C" (poor), and the evaluation result of the seizure load was "C" (poor).

Comparative Example 2

1 part by mass of exfoliated graphene (thickness: 10 to 100 nm, plate area: 1 to 10 μm, specific surface area: 10 m$^2$/g) and 19 parts by mass of Cosmo Pure Spin D (manufactured by Cosmo Oil Lubricants Co., Ltd.) were placed in a container and dispersed with an ultrasonic irradiation device for 7 hours. 30 parts by mass of Diana Fresia (registered trademark) W-90 (manufactured by Idemitsu Kosan Co., Ltd., kinematic viscosity at 40° C.: 95 mm$^2$/s) was added to 20 parts by mass of the obtained dispersion liquid as a base oil, and the mixture was further dispersed by an ultrasonic treatment device for 1 hour to prepare a lubricating composition according to Comparative Example 2 containing a dispersion liquid.

The lubricating composition according to Comparative Example 2 was subjected to a shell four-ball load carrying capacity test in the same manner as in Example 1. In (Test A), the maximum load at which no friction marks having a width of 0.4 mm or more appeared was 50 kgf. In (Test B), the maximum load at which seizure did not occur was 300 kgf. That is, the evaluation result of the friction mark load was "B" (general), and the evaluation result of the seizure load was "B" (general).

(Dispersibility)

0.05 parts by mass of the exfoliated graphene used in Comparative Example 2, 0.5 parts by mass of a dispersant (Unidic R-2000PG manufactured by DIC Corporation), and 9.5 parts by mass of acetone were placed in a glass container and dispersed with an ultrasonic irradiation device for 7 hours. Then, the dispersion liquid was allowed to stand for 3 days, during which the light transmittance and the back light scattering intensity were measured in the vicinity of the center of the glass container using a stability tester (ST-1) (manufactured by EKO) to evaluate the precipitation of the particles, and as a result, the light transmittance gradually increased, the back light scattering intensity gradually decreased, and the precipitation of the particles was observed. That is, the dispersibility of the exfoliated graphene used in Comparative Example 2 in a low-viscosity liquid was "C" (poor).

Comparative Example 3

1 part by mass of commercially available molybdenum disulfide (MoS$_2$) particles (molybdenum sulfide reagent manufactured by Kanto Chemical Co., Inc.) and 19 parts by mass of Cosmo Pure Spin D (manufactured by Cosmo Oil Lubricants Co., Ltd.) were placed in a container and dispersed with an ultrasonic irradiation device for 7 hours. 30 parts by mass of Diana Fresia (registered trademark) W-90 (manufactured by Idemitsu Kosan Co., Ltd., kinematic viscosity at 40° C.: 95 mm$^2$/s) was added to 20 parts by mass of the obtained dispersion liquid as a base oil, and the mixture was further dispersed by an ultrasonic treatment device for 1 hour to prepare a lubricating composition according to Comparative Example 3 containing a dispersion liquid.

The lubricating composition according to Comparative Example 3 was subjected to a shell four-ball load carrying capacity test in the same manner as in Example 1. In (Test A), the maximum load at which no friction marks having a width of 0.4 mm or more appeared was 100 kgf. In (Test B), the maximum load at which seizure did not occur was 300 kgf. That is, the evaluation result of the friction mark load was "A" (good), and the evaluation result of the seizure load was "B" (general).

FIG. 4 shows a result of an X-ray diffraction pattern of the commercially available molybdenum disulfide (MoS$_2$) particles (molybdenum sulfide reagent manufactured by Kanto Chemical Co., Ltd.) used in Comparative Example 3 together with a diffraction pattern of molybdenum sulfide having a 2H crystal structure described in the inorganic crystal structure database (ICSD). It was found that the molybdenum sulfide reagent according to Comparative Example 3 was a molybdenum sulfide having a 2H crystal structure of 99% or more. Half widths of the peak in the vicinity of 39.5° and the peak in the vicinity of 49.5° were as narrow as 0.23° and 0.22°, respectively.

Further, for the commercially available molybdenum disulfide ($MoS_2$) particles (molybdenum sulfide reagent manufactured by Kanto Chemical Co., Ltd.) used in Comparative Example 3, the specific surface area (SA), the ratio (I/II) of the peak intensity I caused by Mo—S to the peak intensity II caused by Mo—Mo obtained based on measurement of the extended X-ray absorption fine structure (EXAFS) of the K absorption edge of molybdenum, and the median diameter $D_{50}$ were determined in the same manner as in the molybdenum sulfide particles according to Synthesis Example 1. Results are shown in Table 1.

molybdenum disulfide ($MoS_2$) particles used in Comparative Example 3 in a low-viscosity liquid was "C" (poor).

The above evaluation results are shown in Table 2 and summarized below.

The lubricating composition using the exfoliated graphene according to Comparative Example 2 is superior to the lubricating oil according to Comparative Example 1 in both the maximum load at which no friction marks appeared and the maximum load at which seizure did not occur, but friction marks are still likely to occur, and seizure is likely to occur at a low load.

The lubricating composition using the commercially available molybdenum disulfide ($MoS_2$) particles according to Comparative Example 3 is superior to the lubricating oil according to Comparative Example 1 in both the maximum load at which no friction marks appeared and the maximum load at which seizure did not occur, and is excellent in that friction marks are less likely to occur, but seizure is likely to occur at a low load.

The lubricating composition according to Example 1 using the molybdenum sulfide particles according to Synthesis Example 1 is superior to the lubricating oil according to Comparative Example 1 in both the maximum load at which no friction marks appeared and the maximum load at which seizure did not occur, is as excellent as the lubricating composition using the commercially available molybdenum disulfide ($MoS_2$) particles according to Comparative Example 3 in that friction marks are less likely to occur, and is excellent in that seizure is less likely to occur even when a high load was applied.

TABLE 1

| | 2H- | 3R- | Conversion rate to $MoS_2$ | By-product | Half width/° In the vicinity of 39.5° | Half width/° In the vicinity of 49.5° | SA/ $m^2 \cdot g^{-1}$ | EXAFS ratio (I/II) | D50/ nm | TEM |
|---|---|---|---|---|---|---|---|---|---|---|
| Synthesis Example 1 | Yes | Yes | 99%< | N.D. | 2.36 | 3.71 | 67.8 | 1.2 | 170 | Sheet shape or nano-ribbon shape |
| Comparative Example 3 | Yes | No | — | — | 0.23 | 0.22 | 5.6 | 0.7 | 13340 | Indefinite shape |

Figure 7:
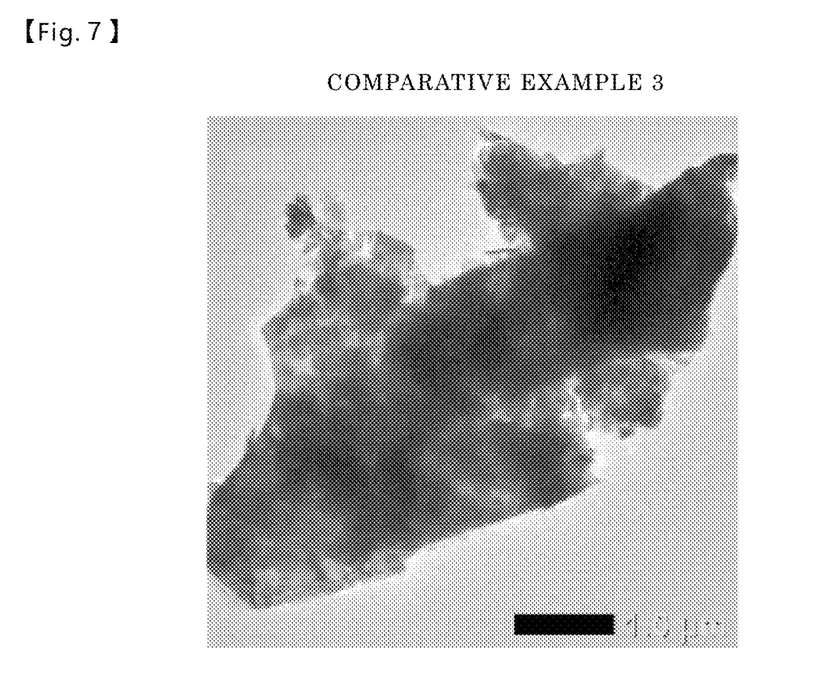
FIG. 7 is a TEM image of the molybdenum sulfide particles according to Comparative Example 3.

FIG. 7 is a TEM image of the molybdenum disulfide ($MoS_2$) particles used in Comparative Example 3. The particle shape was indefinite, and no ribbon-shaped or sheet-shaped molybdenum sulfides were observed.

(Dispersibility)

0.05 parts by mass of the molybdenum disulfide ($MoS_2$) particles used in Comparative Example 3, 0.5 parts by mass of a dispersant (Unidic R-2000PG manufactured by DIC Corporation), and 9.5 parts by mass of acetone were placed in a glass container and dispersed with an ultrasonic irradiation device for 7 hours. Then, the dispersion liquid was allowed to stand for 3 days, during which the light transmittance and the back light scattering intensity were measured in the vicinity of the center of the glass container using a stability tester (ST-1) (manufactured by EKO) to evaluate the precipitation of the particles, and as a result, the light transmittance gradually increased, the back light scattering intensity gradually decreased, and the precipitation of the particles was observed. That is, the dispersibility of the

TABLE 2

| | | | Example 1 | Comparative Example 1 | Comparative Example 2 | Comparative Example 3 |
|---|---|---|---|---|---|---|
| Test A | Maximum load at which no friction marks appeared | kgf | 80 | 40 | 50 | 100 |
| | Evaluation result of friction mark load | | A | C | B | A |
| Test B | Maximum load at which seizure did not occur | kgf | 400 | 130 | 300 | 300 |
| | Evaluation result of seizure load | | A | C | B | B |
| Dispersibility of particles in low-viscosity liquid | | | A | No correspondence | C | C |

Evaluation result of friction mark load: A 80 to 100 (kgf), B 50 to 60 (kgf), C 40 (kgf)
Evaluation result of seizure load: A 350 to 400 (kgf), B 300 (kgf), C 130 (kgf)

REFERENCE SIGNS LIST

1: Production apparatus
2: Calcining furnace
3: Cooling pipe

4: Collection device
5: Discharge port
6: Opening degree adjustment damper
7: Observation window
8: Air-exhaust device
9: External cooling device

The invention claimed is:

1. A lubricant comprising molybdenum sulfide particles, wherein
the molybdenum sulfide particles contain molybdenum disulfide having a 2H crystal structure and a 3R crystal structure,
the molybdenum sulfide particles have a specific surface area of 10 m$^2$/g or more, the specific surface area being measured by a BET method, and
in a spectrum of the molybdenum sulfide particles obtained from powder X-ray diffraction (XRD) using Cu-K$\alpha$ rays as an X-ray source, both a peak in a vicinity of 39.5° and a peak in a vicinity of 49.5° include a synthetic peak of the 2H crystal structure and the 3R crystal structure, and a half width of the peak in the vicinity of 39.5° and a half width of the peak in the vicinity of 49.5° is 1° or more.

2. The lubricant according to claim 1, wherein the specific surface area of the molybdenum sulfide particles is 30 m$^2$/g to 300 m$^2$/g, the specific surface area being measured by a BET method.

3. The lubricant according to claim 1, wherein
the molybdenum sulfide particles have a median diameter $D_{50}$ of 10 nm to 1,000 nm, the median diameter $D_{50}$ being determined by a dynamic light scattering type particle diameter distribution measuring device.

4. The lubricant according to claim 1, wherein
in a radial distribution function of the molybdenum sulfide particles obtained from an extended X-ray absorption fine structure (EXAFS) spectrum of a K absorption edge of molybdenum, a ratio (I/II) of peak intensity I caused by Mo—S to peak intensity II caused by Mo—Mo is more than 1.0.

5. A lubricating composition comprising:
molybdenum sulfide particles which are the lubricant according to claim 1; and
a base oil which is a mineral oil, a synthetic oil, or a partially synthetic oil.

6. The lubricating composition according to claim 5, wherein
the molybdenum sulfide particles, which are the lubricant, are contained in an amount of 0.0001% by mass to 50% by mass with respect to 100% by mass of the total mass of the lubricating composition.

* * * * *